(12) United States Patent
Osypka Rubenstein et al.

(10) Patent No.: US 8,388,634 B2
(45) Date of Patent: Mar. 5, 2013

(54) DEVICE FOR CONNECTING TWO BLOOD VESSELS

(76) Inventors: Nicola Osypka Rubenstein, Munich (DE); Eckhard Alt, Munich (DE)

( * ) Notice: Subject to any disclaimer, the term of this patent is extended or adjusted under 35 U.S.C. 154(b) by 339 days.

(21) Appl. No.: 12/599,627

(22) PCT Filed: May 7, 2008

(86) PCT No.: PCT/EP2008/003669
§ 371 (c)(1),
(2), (4) Date: Aug. 5, 2010

(87) PCT Pub. No.: WO2008/138529
PCT Pub. Date: Nov. 20, 2008

(65) Prior Publication Data
US 2010/0324653 A1    Dec. 23, 2010

(30) Foreign Application Priority Data
May 11, 2007   (DE) .......................... 10 2007 022 060

(51) Int. Cl.
*A61B 17/08* (2006.01)
(52) U.S. Cl. ....................................... 606/153
(58) Field of Classification Search .................. 606/108, 606/151, 153, 191, 213, 215; 623/1.11, 1.12, 623/1.15, 1.16, 1.22, 1.36
See application file for complete search history.

(56) References Cited

U.S. PATENT DOCUMENTS

| 4,721,109 | A | | 1/1988 | Healey |
| 5,061,275 | A | * | 10/1991 | Wallsten et al. ............. 623/1.22 |
| 5,591,226 | A | * | 1/1997 | Trerotola et al. ............ 623/1.12 |
| 5,755,775 | A | | 5/1998 | Trertola et al. |
| 5,876,432 | A | * | 3/1999 | Lau et al. ..................... 623/1.16 |
| 6,485,513 | B1 | | 11/2002 | Fan |
| 6,517,573 | B1 | * | 2/2003 | Pollock et al. ............... 623/1.15 |
| 2006/0271164 | A1 | | 11/2006 | Shaolian et al. |

FOREIGN PATENT DOCUMENTS

| WO | 9819631 | 5/1998 |
| WO | 9913808 | 3/1999 |
| WO | 9965420 | 12/1999 |
| WO | 2007016166 | 2/2007 |

* cited by examiner

*Primary Examiner* — Julian Woo
(74) *Attorney, Agent, or Firm* — Volpe and Koenig, P.C.

(57) ABSTRACT

A device for connecting abutting ends (1) of two blood vessels (2) that will be continuous after being mutually connected (anastomosis), the device primarily and substantially including a supporting part (3) that can be inserted in the two ends (1) of the blood vessel (2) to be connected, made, for example, of plastic or metal, particularly in the form of a mesh, grid, or cage. The supporting part (3) can be inserted into the blood vessels (1) far enough that the faces (4) of the blood vessel ends (1) can be brought into contact with each other and are in contact with each other in the usage position. The outer cross-section of the supporting part (3) in the usage position is thereby approximately the same as the inner cross-section of the blood vessel (1) in question and has an inner pass-through cross-section (lumen), so that blood can flow unhindered, but the blood vessels (1) in contact with each other are fixed at the same height to each other on the inside, and secured against sideways deflection relative to each other or sideways deflection of the blood vessel walls. The supporting part (3) can be made from one or two pieces.

13 Claims, 2 Drawing Sheets

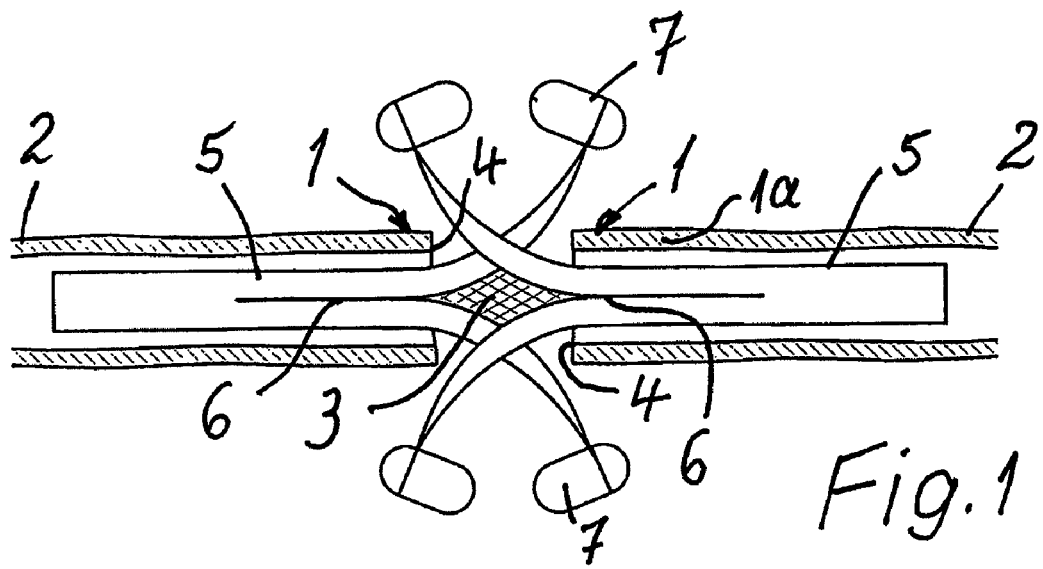
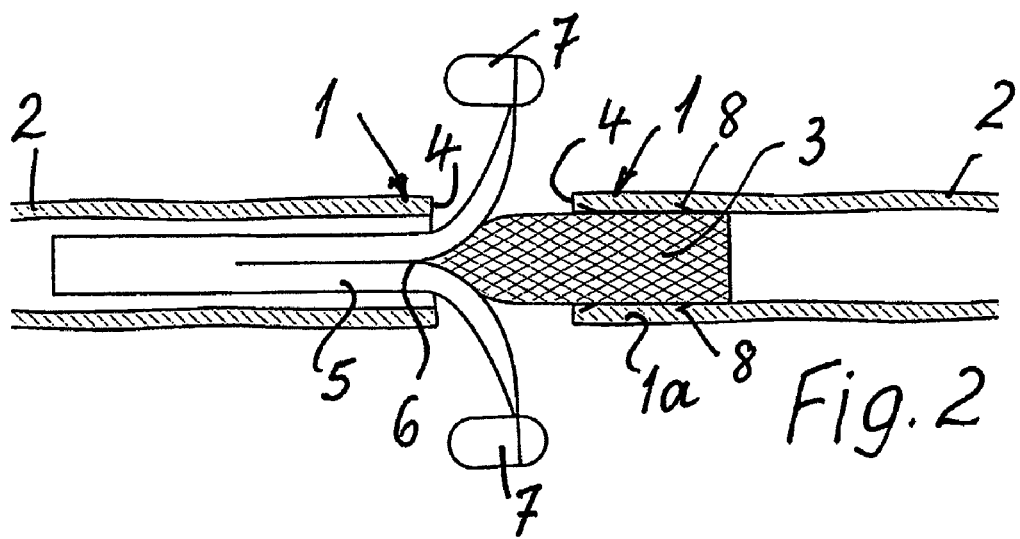
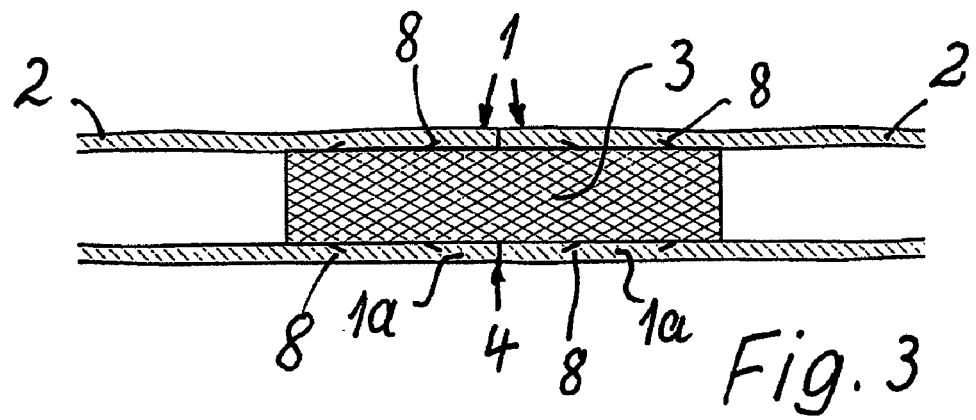

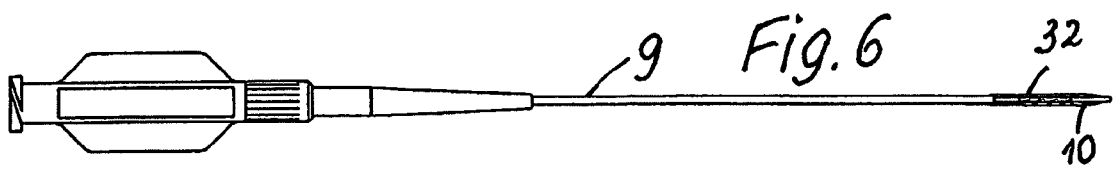
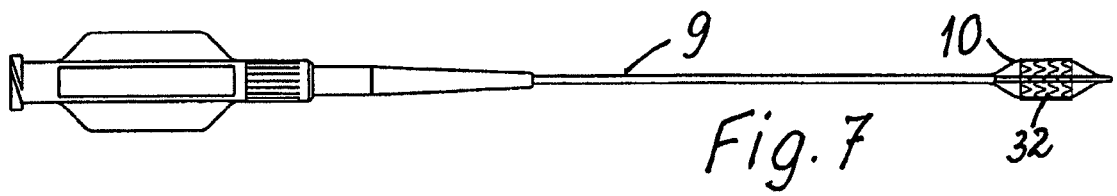
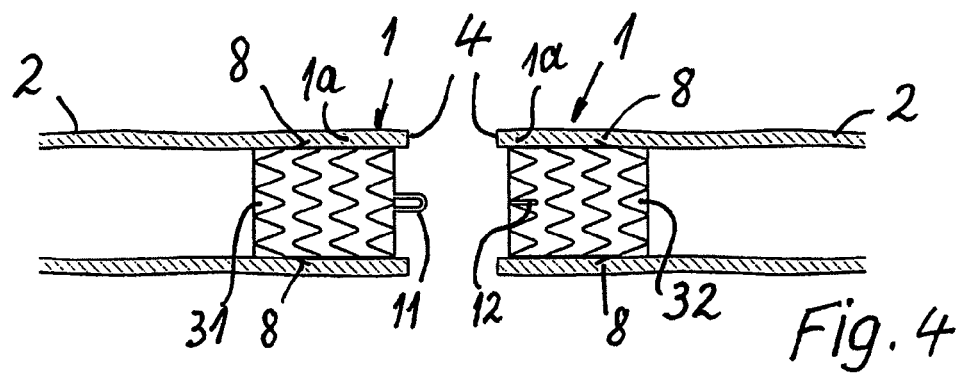
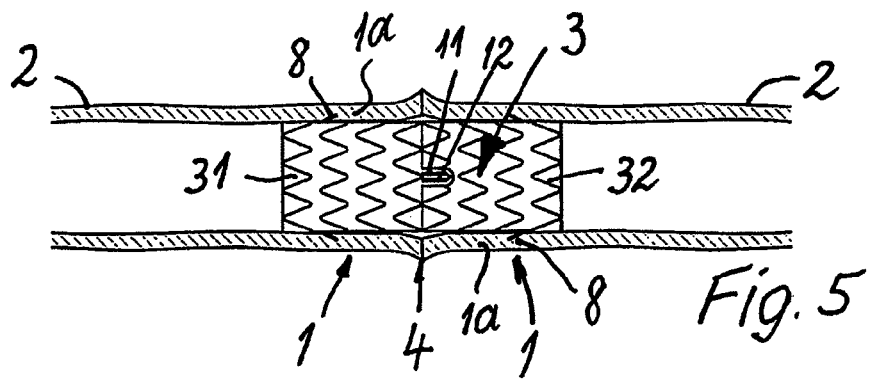

ns into one of the blood-vessel ends to be mutually connected.

DEVICE FOR CONNECTING TWO BLOOD VESSELS

BACKGROUND

The invention relates to a device for connecting abutting ends of two blood vessels that will be continuous after being mutually connected (anastomosis), wherein the device comprises a support part that can be inserted and that can automatically expand in the two ends of the blood vessels to be connected and that is made from a mesh or grid or cage with a lumen passing through the inside. In addition, in the position of use, the outer cross section of the support part corresponds approximately to the inner cross section of the respective blood vessel end supported by this part.

Micro-vascular anastomosis, that is, the connection of two blood-vessel ends, is one of the most difficult tasks in plastic surgery, with technical problems in the connection of the blood vessels leading to a high percentage of failures. An efficient and safe execution of this procedure reduces the time and the associated risk of exsanguination of the tissue and also reduces the risk of thrombosis and obstacles to the passage of blood caused by exsanguination.

In comparison with certain devices that require considerable deformation of the blood-vessel ends to be connected, it is to be viewed as favorable if the two ends of the blood vessels can abut each other and can be, for example, sutured together. Such suturing, however, is difficult due to the considerable flexibility of the blood-vessel walls and requires a large amount of skill.

Indeed, from WO2007016166 A2, a closure is known with which an opening within a blood vessel can be closed blood-tight, but here no support part made exclusively from a mesh or grid or cage is provided, because such a support part would not be blood-tight. The removal of a sleeve initially holding the device to a smaller cross section when it is inserted into two blood-vessel ends that can be brought together would be difficult or impossible.

SUMMARY

Therefore, there is the objective of creating a device for connecting abutting blood-vessel ends, wherein this connection can be performed easily and quickly with this device and, for example, eversion at the free vessel ends can be avoided. Here, the support part should be able to be easily inserted into the blood-vessel ends or the blood-vessel ends should be able to be pushed easily onto this support part initially having a reduced cross section.

For meeting this objective, the device noted above is characterized in that the support part is enclosed on each of its two regions that can be inserted into blood-vessel ends by a removable ring or tubular piece or fibrous sleeve and is held to a reduced cross section and that the tubular pieces, rings, or fibrous sleeves can be removed one after the other.

Therefore it is possible with the help of the support part according to the invention to support the two blood-vessel ends from the inside and to connect these ends for their mutual contact in an arbitrary way, for example, by suturing. An important advantage of the support by the support part from the inside here is that the blood-vessel ends and/or their walls, on one hand, cannot bulge out and, on the other hand, also do not have to be everted or expanded unnecessarily, although a certain slight amount of expansion is conceivable for a secure inner support.

Here, the support part can be made from plastic or metal, in particular, from a mesh or grid. In this way the insertion of suturing material at the connection point is simplified. Due to the attachment of removable rings or tubular pieces or fibrous sleeves at the two regions that can each be inserted into one blood-vessel end, the support part can be easily inserted into the blood-vessel ends or the blood-vessel ends can be easily pushed over this support part still having a reduced cross section. The removal of the ring or tubular piece or fibrous sleeve can be performed after the insertion into one of the blood-vessel ends, that is, one after the other. Thus, one region of the support part can initially and automatically support the associated blood-vessel end in its position of use in this blood-vessel end, after which the same can be performed with the other region at the other blood-vessel end.

In the case of a preferred embodiment of the invention, the support part of the device can have a one-piece construction and can be inserted with corresponding parts of its longitudinal extent into the two blood-vessel ends before these blood-vessel ends are moved together into their touching position. This produces a large degree of safety against mutual, lateral displacement of the blood-vessel ends when they are connected.

The tubular piece or pieces can have an intended tear point and gripping region or handholds, in particular, on both sides of this intended tear point. This simplifies the removal of the tubular pieces after the positioning of the support part, although this engages in both blood-vessel ends. The tubular pieces can be torn and removed from the side, after which the blood-vessel ends can be finally pushed together.

However, it is also possible that the support part is made from plastic, stainless steel, stainless-steel alloy, shape-memory material, shape-memory metal, or Nitinol and can be inserted into the blood-vessel ends in a state of reduced cross section and can be automatically adapted to the inner cross section of the blood-vessel ends through the shape-memory effect of its material. Thus, in this case, leading the two blood-vessel ends together with the support part inserted therein can also be performed easily, after which, due to an automatic expansion of the support part, the blood-vessel ends are secured in the continuous position against mutual, lateral bulging.

Here, the previously mentioned measures can also be combined, that is, a support part made, for example, from Nitinol mesh can also be held together initially by one or two tubular pieces until the support part is positioned sufficiently, in order to remove the tubular pieces and to bring the vessel ends into touching contact.

Another or additional possibility is that the support part is held on the sections that can be inserted into the two blood-vessel ends by at least one fibrous sleeve to the smaller diameter and can be opened through unwinding or separation of the fibrous sleeve.

If possible, mutual suturing of the blood-vessel ends can be avoided in that barbed-hook-like projections acting opposite each other are provided on the two support part regions and these projections extend starting from the outside of the support part in the direction toward the corresponding blood-vessel end, that is, in the direction toward each other. If the blood-vessel ends are pushed over such a support part and, in this way, assembled and guided optionally with their ends still somewhat under pressure, the barbs can grip each of the blood-vessel ends on the inside and also can be fixed in the axial direction in the mutual contact position, so that they can grow together.

A modified embodiment of the support part according to the invention can have considerable and advantageous meaning in that the support part has a two-part construction and each individual part of the support part can be inserted or fits into one of the blood-vessel ends. In this way it is also prevented that, in the case of the mutual connection of the blood-vessel ends touching on the ends, these ends or their walls can bulge.

Here it is especially favorable when the two individual parts of the support part can be connected or coupled mechanically to each other in the position of use. In this way, they can be initially inserted into the blood-vessel ends and then can be guided and connected together with these ends, which can also lead simultaneously to the touching contact of the blood-vessel ends that are then already connected or through additional measures such that they can grow together. For example, they could be sutured together or connected in some other way or can be held in touching contact by the connection of the two individual parts of the support part, in order to grow together.

In the case of a useful embodiment of the device according to the invention with a support part made from two individual parts that can be coupled to each other, the connection or coupling parts of at least one of the edges or end faces of this individual part facing opposite the two individual parts of the support part can project so far that they are connected to the counter parts on the other individual part for end faces of the blood-vessel ends that abut each other or are pressed against each other in the position of use.

At this point it should be mentioned that the support part, whether it is formed in one piece or from two individual parts that can be coupled together, has an inner lumen or a continuous inner longitudinal hollow space and contacts only on the inside to the wall of the blood vessels whose cross section, incidentally, is largely left open.

The projecting connection or coupling parts arranged for mutual coupling or connection to the support part thus similarly run, to a large extent, in the region of the inside of the blood vessels and at a cross section or diameter that is left open by the support part in its interior.

Here it is favorable when eyelets are provided on one individual part and matching hooks are provided on the other individual part for coupling the two individual parts of the support part, wherein, in the position of use, these hooks engage or snap into the eyelets. By bringing the two individual parts together with the blood-vessel ends supported by these parts, the mutual connection is realized practically automatically.

The two individual parts of the two-part support part can be expandable, cage-like plastic, metal, or stainless-steel pieces that are pressed together and can be inserted independently from each other into the respective open ends of the blood vessel to be connected.

While in the case of a one-piece support part the mutual bulging of the blood-vessel ends is easily prevented, the two-part construction of the support part has the advantage that its individual parts can be inserted more easily into the blood-vessel ends.

The individual parts of the two-part support part can be expanded at its position of use after insertion into the respective blood-vessel end by means of an expansion aid or balloon catheter or due to a production from a shape-memory material, e.g., Nitinol.

For axial fixing of the blood-vessel ends in the brought-together position away from their touching region, the individual parts of the two-part support part can have barbs or projections on the outside for the positive-fit fixing within the blood-vessel ends. Also, in the case of a two-part construction of the support part, such barb-like projections could be provided for the axial fixing of the blood-vessel ends, so that, after the mutual connection of the individual parts through suturing or through mechanical coupling, the blood-vessel ends are also fixed in the axial direction.

Here, it is also conceivable to insert the individual parts of the support part so deep into the blood-vessel ends that they can be coupled to each other, but the blood-vessel ends project slightly past these individual parts or past at least one of the individual parts, so that they are also located under a certain amount of mutual pressure in the case of mutual touching contact, which improves the mutual sealing and promotes growing together.

The support part that is made from plastic, metal mesh, or a metal grid and that has, in particular, a cage-like shape can be coated—whether it is one piece or is made from two individual parts—at least in some regions, for example, with iridium oxide, carbon, pharmaceutical or medicinal agents, or molecular-biological products. Through such coating, the healing process and the growing together of the vessel ends can be promoted. Optionally, additional medicinal effects can also be achieved in this way.

Primarily for the combination of individual or several of the previously described features and measures, a device is produced that is provided, primarily, as a one-part support part in an initially pressed-together form and can be inserted in this form into the blood-vessel ends, wherein it can be held in its middle, for example, by a forceps-like device and can be manipulated with this device until it is inserted into both open ends of the two vessels. The connection of the two blood-vessel ends can be fixed, if necessary, by pin-holing before the support part is released for self-expansion. The fixing of the support part to the walls of the blood vessels can be performed with barb-like projections or hook anchors arranged on this support part.

For the use of a support part made from two individual parts, these can be inserted, in particular, independently from each other, in turn, in pressed-together form into the respective open end of the blood vessel to be connected. With an expansion aid or through self-expansion, the individual parts can be expanded to the needed diameter, wherein they open and maintain, like a one-piece support part, an inner cross section in the blood vessel. After the mutual bringing together, they can be connected and, for example, hooked to each other, which causes anastomosis of the blood vessels lying above and surrounding the individual parts of the support part. The fixing can be realized, in turn, through barb-like projections or on the individual parts of integrated hook anchors.

BRIEF DESCRIPTION OF THE DRAWINGS

Below, embodiments of the invention are described in more detail with reference to the drawing. Shown in—in part considerably—schematized representation are:

FIG. 1 a longitudinal section view through two vessel ends to be connected to each other, wherein a device according to the invention in the form of a one-piece support part—comprising tubular pieces on the outside fixing its cross section to a reduced form—is already inserted for the most part into these two blood-vessel ends, FIG. 2 a view according to FIG. 1, wherein the tube keeping the cross section reduced is removed from the region of the support part inserted into one of the blood-vessel ends, while the other part is still held together by a corresponding tubular piece in the other blood-vessel end, FIG. 3 a view according to FIGS. 1 and 2 after the removal of both tubular pieces and the pushing together of the two blood-vessel ends onto the outside of the one-piece support part that contains an inner lumen and that holds the two blood-vessel ends together with barb-like projections, FIG. 4 a view similar to FIG. 2 of a modified embodiment in which the support part belonging to the device or forming the device has a two-part construction and each individual part of this two-part support part is inserted into one of the vessel ends to be connected, FIG. 5 a view similar to FIG. 3 after the mutual connection or coupling of the individual parts of the two-part support part, wherein the end faces of the vessel ends to be connected are led into tight touching contact with each other, FIG. 6 a view of a balloon catheter for application to the individual parts of the support part, wherein the individual part has a still reduced cross section, and FIG. 7 a view according to FIG. 6, after the expansion of the individual parts of the support part, which, when it is used, takes place after the insertion into the blood-vessel ends.

DETAILED DESCRIPTION OF THE PREFERRED EMBODIMENTS

In the following description of two different embodiments of a device for connecting abutting ends 1 of two blood vessels 2 that will be continuous after being mutual connected, parts matching in function are indicated with matching reference numbers even for modified constructions and shapes.

The essential part of the mentioned device is a support part 3 that can be inserted into the two ends 1 of the blood vessel 2 to be connected (cf. FIGS. 3 and 5).

According to FIGS. 3 and 5, this support part 3 can be inserted so far into the ends 1 of the blood vessel 2 to be connected that the end faces 4 of the blood-vessel ends 1 can be brought into touching contact with each other or these have touching contact according to FIGS. 3 and 5.

Here, in the position of use, the outer cross section of the support part 3 corresponds approximately to the inner cross section of each blood vessel 2 or each blood vessel end 1 and therefore the touching blood-vessel ends 1 and their walls 1a are fixed in the position of use according to FIGS. 3 and 5 at the same height to each other without lateral bulging.

The support part 3 can be made here from plastic or metal, in particular, from a mesh or grid, as indicated in the two embodiments in different shapes.

In FIGS. 1 to 3, an embodiment is shown in which the support part 3 has a one-piece construction and can be inserted with each part or a half of its longitudinal extent into the two blood-vessel ends 1—according to FIGS. 1 and 2 before its moving together into its touching position according to FIG. 3.

Here, one recognizes primarily in FIG. 1 that this support part 3 is surrounded by a removable tubular piece 5 on each of its two regions that can be inserted into the blood-vessel ends 1 and is kept to a smaller cross section than the inner cross section of the blood-vessel ends 1, in order to simplify this mutual insertion, for example, with the help of a forceps-like instrument engaging approximately in the center of the support part 3. Instead of tubular pieces 5, a separable or removable ring or a fibrous sleeve could also be provided.

According to FIGS. 1 and 2, the tubular pieces 5 have an intended tear point 6 running in the axial direction and, on both sides of this tear point, gripping regions or handholds 7, so that the tubular pieces can be easily torn after pushing on the blood-vessel end 1 or inserting the support part 3 with its two insert regions into the blood-vessel ends 1 and can be moved away to the side, wherein these processes can take place successively according to FIGS. 1 to 3. Initially, one tubular piece 5 can be peeled, that is, torn and moved away laterally, wherein one region of the support part 3 expands automatically into its position of use and supports the corresponding vessel end 1 on the inside. Then the same happens with the second tubular piece 5, wherein the inner support of the support part 3 allows the blood-vessel ends 1 to be pushed together.

Here it will be recognized that barb-like projections 8 that act against each other on both support part regions and that extend starting from the outside of the support part 3 in the direction toward the respective blood-vessel end 1 or toward the end face 4, that is, in the direction toward each other. So that the blood-vessel ends 1 can be shifted in the axial direction over these projections 8, however, movement in the opposite direction is prevented, which already leads to a mutual connection of the blood-vessel ends 1. In addition, with suturing material, for example, initially with the first sub-position according to FIG. 2 can be fixed and/or the end position according to FIG. 3 can likewise also be secured additionally with suturing material. If necessary, the barb-like projections 8 could also be eliminated and the mutual connection of the blood-vessel ends 1 at their end faces 4 can be performed only with suturing material. In each case, the blood-vessel ends 1 are prevented from bulging relative to each other in the lateral direction or also only their walls 1a, because the support part 3 fixes the blood-vessel ends 1 in the position of use against such bulging movements.

FIGS. 4 to 7 show a two-part support part 3, wherein, according to FIGS. 4 and 5, each individual part 31 and 32 of the support part 3 can be inserted and fits into one of the blood-vessel ends. In the position of use according to FIG. 5, the two individual parts 31 and 32 of the support part 3 are connected to each other and mechanically coupled in a manner still to be described.

For inserting these individual parts 31 and 32 into the associated blood-vessel end 1, a balloon catheter 9 shown schematized in FIGS. 6 and 7 can be used, wherein FIG. 6 holds, on the end balloon 10 of the balloon catheter 9, an individual part 31 or 32 still having a small outer cross section, wherein this part can be expanded according to FIG. 7 with the help of the balloon 10, but only after insertion into one of the blood-vessel ends 1.

In FIG. 4, it will be recognized that the connection or coupling parts 11 of the one individual part 31 of the support part 3 projects relative to its edge facing the other support part 32 or the end face of this individual part 31 so far that it is connected to counter parts 12 on the other individual part 32 in the position of use for end faces 4 of the blood-vessel ends 1 abutting or pressed against each other according to FIG. 5. Here, for coupling the two individual parts 31 and 32 of the support part 3 on the one individual part 31, eyelets 11 preferably distributed on the periphery are provided and on the other individual part 32, matching hooks 12 arranged within its longitudinal extent are provided as counter parts to the eyelets 11, wherein these hooks are engaged or snapped into the eyelets 11 in the position of use. Here, on the periphery of the individual parts 31 and 32, several such eyelets 11 and hooks 12 could be distributed, but preferably at least at two opposing positions on a diameter line.

In FIGS. 4 and 5 it is indicated that the individual parts 31 and 32 can be inserted so deep into the blood-vessel ends 1 that these project in the axial direction slightly opposite these individual parts 1 and 2, so that, according to FIG. 5, they contact each other through the mutual coupling of the individual parts 31 and 32 with some pressure on their end faces 4 and, if necessary, can bulge somewhat, as shown somewhat exaggerated in FIG. 5, in order to achieve the tightest possible connection.

As already mentioned, the two individual parts 31 and 32 of the two-part support part 3 could initially have a small cross section and extent according to FIG. 6 and could be made from expandable material, such as plastic, metal, or stainless steel, and could be inserted independently from each other with the help of the balloon catheter 9 into the respective open end 1 of the blood vessel 2 to be connected, after which they can be expanded to their position of use according to FIG. 4 with the help of the balloon catheter 9 or some other expansion element or due to production from a shape-memory material, e.g., from Nitinol.

The individual parts 31 and 32 of the two-part support part 3 have barbs or projections 8 on the outside for the positive-fit fixing within the blood-vessel ends 1, wherein these barb-like projections 8 likewise extend starting from the outside of the support part 3 in the direction toward the respective blood-vessel end 1 or the end face 4, that is, toward each other.

It should also be mentioned that the support part 3 that has, in particular, a cage-like shape and that is made from plastic, metal mesh, or a metal grid, whether it has a one-piece or two-piece construction, could be coated at least in some regions, indeed, for example, with iridium oxide, carbon, pharmaceutical or medicinal agents, or molecular-biological products, in order to achieve, primarily, medicinal effects.

The device for connecting abutting ends 1 of two blood vessels 2 that will be continuous after being mutually connected (anastomosis) has primarily and essentially a support part 3 that can be inserted into the two ends 1 of the blood vessel 2 to be connected and that is made, for example, from plastic or metal, in particular, in the form of a mesh or grid or cage. The support part 3 can be inserted so far into the blood-vessel ends 1 that the end faces 4 of the blood-vessel ends 1 can be brought into touching contact with each other and have touching contact in the position of use. Here, the outer cross section of the support part 3 corresponds in the position of use approximately to the inner cross section of the respective blood vessel 1 and has an inner passage cross section (lumen), so that the blood can flow unimpaired, but the touching blood-vessel ends 1 are fixed at the same height to each other on the inside and against lateral bulging relative to each other and/or against lateral bulging of the blood-vessel walls 1a. The support part 3 can here have a one-piece or two-piece construction.

The invention claimed is:

1. Device for connecting abutting ends (1) of two blood vessels (2) that will be continuous after being mutually connected, comprising a support part (3) that can expand automatically and that is insertable into the two ends (1) of the blood vessels (2) to be connected and that is made from a mesh or grid or cage with an inner, continuous lumen, wherein an outer cross section of the support part (3) approximately corresponds in a position of use to an inner cross section of the respective blood-vessel end (1) to be connected, the support part (3) is enclosed at each of two regions thereof that are adapted for insertion into the blood-vessel ends (1) by a removable ring or tubular piece (5) or fibrous sleeve and held to a reduced cross section and the tubular pieces (5), rings, or fibrous sleeves are removable, and the support part (3) has a two-part construction with two individual parts (31, 32), each of which is adapted to be inserted or fits into one of the blood-vessel ends (1).

2. Device according to claim 1, wherein the tubular pieces (5) have an intended tear point (6).

3. Device according to claim 2, wherein the tubular pieces (5) have gripping regions or handholds (7) on both sides of the intended tear point (6).

4. Device according to claim 1, wherein the support part (3) is made from plastic, stainless steel, stainless steel alloy, shape-memory material, shape-memory metal, or Nitinol and is insertable in a state of reduced cross section into the blood-vessel ends (1) and can be automatically adapted to the inner cross section of the blood-vessel ends (1) through a shape-memory effect of the material.

5. Device according to claim 1, wherein the support part (3) is held to a smaller diameter at sections that can be inserted into the two blood-vessel ends (1) by a fibrous sleeve and can be released by unwinding or separating the fibrous sleeve.

6. Device according to claim 1, wherein barb-like projections (8) acting in opposite directions from each other are provided on the two support-part regions and extend starting from an outside of the support part (3) in a direction toward a middle portion thereof that is adapted to hold the respective blood-vessel ends (1).

7. Device according to claim 1, wherein the two individual parts (31, 32) of the support part (3) are connectable to each other or can be coupled mechanically with a connection or coupling parts in a position of use.

8. Device according to claim 7, wherein the connection or coupling parts (11) of at least one of the two individual parts of the support part (3) project beyond facing edges or end faces of a first one of the individual parts (31) so that, in the case of abutting or pressed-together end faces (4) of the blood-vessel ends (1), they are connected to counter parts (12) on the other of the individual parts (32) in the position of use.

9. Device according to claim 7, wherein for coupling the two individual parts (31, 32) of the support part (3), eyelets (11) are provided on one of the individual parts (31) and matching hooks (12) are provided on the other individual part (32), wherein the hooks engage or snap into the eyelets (11) in the position of use.

10. Device according to claim 1, wherein the two individual parts (31, 32) of the two-part support part (3) are expandable, cage-like plastic, metal, or stainless-steel pieces that are pressed together and are adapted to be inserted independently from each other into the respective open end (1) of the blood vessel (2) to be connected.

11. Device according to claim 10, wherein after insertion, the individual parts (31, 32) of the two-part support part (3) can be expanded to a useful extent thereof by an expansion aid or balloon catheter (9) or due to production from shape-memory material.

12. Device according to claim 1, wherein the individual parts (31, 32) of the two-part support part (3) have outer barbs or projections (8) adapted for positive-fit fixing within the blood-vessel ends (1).

13. Device according to claim 1, wherein the support part (3) has a cage-like shape and is made from plastic, metal mesh, or a metal grid and is coated at least in some regions with iridium oxide, carbon, pharmaceutical or medicinal agents or molecular-biological products.

* * * * *